(12) United States Patent
Huang et al.

(10) Patent No.: US 7,413,770 B2
(45) Date of Patent: Aug. 19, 2008

(54) ETHYLENE GLYCOL MONOLAYER PROTECTED NANOPARTICLES

(75) Inventors: Xueying Huang, Hockessin, DE (US); Ming Zheng, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 464 days.

(21) Appl. No.: 10/630,248

(22) Filed: Jul. 30, 2003

(65) Prior Publication Data

US 2005/0074551 A1    Apr. 7, 2005

Related U.S. Application Data

(60) Provisional application No. 60/400,144, filed on Aug. 1, 2002.

(51) Int. Cl.
*B05D 7/00* (2006.01)

(52) U.S. Cl. .................. 427/216; 427/220; 428/403

(58) Field of Classification Search ................ 427/216, 427/220; 428/403
See application file for complete search history.

(56) References Cited

U.S. PATENT DOCUMENTS

| | | | |
|---|---|---|---|
| 6,074,979 A | 6/2000 | Hagemeyer et al. | |
| 6,521,285 B1 | 2/2003 | Biebuyck et al. | |
| 2002/0034827 A1 | 3/2002 | Singh et al. | |
| 2003/0157260 A1 | 8/2003 | Rubner et al. | |

OTHER PUBLICATIONS

Prime et al., Self-Assembled Organic Monolayers: Model Systems for Studying Adsorption of Proteins at Surfaces, Science, 1991, 252, 5009, 1164-1167.
Lahiri et al., A Study for the Generation of Surfaces Presenting Ligands for Studies of Binding Based on an Active Ester as a Common Reactive Intermediate: A Surface Plasmon Resonance Study, Analytical Chemistry; 1999, Feb. 15, 71(4), 777-790.
Templeton et al., Redox and Fluorophore Functionalization of Water-Soluble, Tiopronin-Proteced Gold Clusters, JACS, 1999, 121, PPG 7081-7089.
Foos et al., Thiol-Terminated Di-, Tri-, and Tetraethylene Oxide Functionalized Gold Nanoparticles: A Water-Soluble, Charge-Neutral Cluster, Chem. Mater. 2002, 14, pp. 2401-2408.
Templeton et al., Water-Soluble, Isolable Gold Clusters Protected byTiopronin and Coenzyme a Monolayers, Langmuir 15: 66-76, 1999.
Chen et al., Poly(N-vinylisobutyramide)-stabilized platinum nanoparticles; synthesis and temperature-responsive behavior in aqueous solution. Colloids and Surfaces A 169: 107-116, 2000.

(Continued)

*Primary Examiner*—Timothy Meeks
*Assistant Examiner*—Jimmy Lin

(57) ABSTRACT

Metallic nanoparticles coated with a mixed monolayer with well defined thickness or length are prepared. The mixed monolayer comprises a capture coating component useful for the specific capture of materials and a shielding coating component for elimination of non-specific binding of materials to the capture component.

14 Claims, 6 Drawing Sheets

Short chain protected gold nanoparticle with one binding ligand

Long chain protected gold nanoparticle with one binding ligand

OTHER PUBLICATIONS

Wuelfing et al., Nanometer Gold Clusters Protected by Surface-Bound Monolayers on Thiolated Poly(ethylene glycol), Polymer Electrolyte, J. Am. Chem. Soc. 120• 12696-12697, 1998.

Chan et al., Quantum Dot Bioconjugates for Ultrasensitive Nonisotopic Detection, Science, 281: pp. 2016-2018, 1998.

Mitchell et al., Programmed Assembly of DNA Functionalized Quantum Dots, J. Am. Chem. Soc. 121: 8122-8123, 1999.

Napper, Steric Stabilization, J. Colloid. Interface. Sci 58: 390-407, 1977.

Prime et al., Adsorption of Proteins onto Surfaces ContainingEnd-Attached Oligo(ethylene oxide): A Model System Using Self-Assembled Monolayers, AJ. Am. Chem. Soc. 1993, 115, 10714-10721.

Brust et al., Synthesis of Thiol-derivatised Gold Nanoparticles in a Two-phase Liquid-Liquid System, Department of Chemistry, University of Liverpool, UK.

Zhang et al., Proteins and cells on PEG immobilized silicon surfaces, Biomaterials 19, 1998, 953-960.

Otsuka et al., Quantitative and Reversible Lectin-Induced Association of Gold Nanoparticles Modified with α-Lactosyl-∞-mercapto-poly(ethylene glycol), J. Am. Chem. Soc. 2001, 123, 8226-8230.

Snow et al., Self-assembly of gold nanoclusters on micro- and nanoelectronic substrates, J. Mater. Chem., 2002, 12, 1222-1230.

Roberts et al., Using Mixed Self-Assembled Monolayers Presenting RGD and (EG)$_3$OH Groups to Characterize Long-Term Attachment of Bovine Capillary Endothelial Cells to Surfaces.

Short chain protected gold nanoparticle with one binding ligand

Long chain protected gold nanoparticle with one binding ligand

Figure 1

Figure 2
Gel image of protein binding assay

Figure 3
Chromatograph results of strong cation exchange chromatography for Au-Tp and Au-EG4 binding with lysozyme Figure 4
Chromatograph of Au-EG4 and Au-Tp particles through a strong anion exchange column Figure 5a
NMR spectra of the free EG4-SH molecule Figure 5b
NMR spectra of Au-S-EG4 nanoparticle Lane 1: 10 µL of Au-EG$_4$ particles at ~ 100 µM, Lane 2 to 3, same amount of Au particles mixed with 5 µg of total RNA and 1 µg of chromosomal DNA, respectively Figure 6
Gel electrophoresis image of a binding assay of Au-EG$_4$ particles with RNA and DNA

ETHYLENE GLYCOL MONOLAYER PROTECTED NANOPARTICLES

This application claims the benefit of U.S. Provisional Application 60/400,144, filed Aug. 1, 2002.

FIELD OF INVENTION

The invention relates to the preparation of metal nanoparticles coated with a mixed monolayer. The mixed monolayer comprises a capture component for the capture of various ligands and a shielding component which acts to block non-specific binding materials to the monolayer.

BACKGROUND

Nanomaterials and their hybrids with biological molecules are recognized to have potential applications in electronic, optics, genomics, proteomics, and biomedical and bioanalytical areas. The usefulness of these hybrid materials largely depends on how well can one achieve rational design based on specific binding between inorganic nanomaterials and biological molecules. It is generally recognized that the surfaces of many nanoparticles, such as Au, Ag, Pt and Cu are charged, which cause non-specific binding with biological molecules via electrostatic interactions. Alkyl thiol protected nanoparticles reduce the electrostatic interactions but induce hydrophobic interactions, another type of non-specific interaction. In addition, alkyl thiol protected nanoparticles are not soluble in water, which makes them non-compatible with biomolecules that require aqueous environment for activity. Prime et al. (*Science* (1991), 252(5009), 1164-7) and Lahiri et al. (*Analytical Chemistry*, 1999 Feb. 15, 71(4) 777-90) both describe a method to prepare a model system for the adsorption of proteins on surfaces by preparing self-assembled monolayers of alkanethiols on gold films. Singh et al. describes a method for using gold nanorods to extract groups of biomolecules, using derivatized alkanethiols (U.S. Patent Appl. 20020034827).

Nanoparticles coated with tiopronin (N-2-mercaptopropionyl-glycine, TP) have the advantage of being water-soluble, but are subject to non-specific binding of biomolecules. Templeton et al. (JACS, 1999, 121, pg 7081) prepared gold clusters coated with single monolayers of tiopronin and acidic, water soluble ligands. Gold and silicon surfaces have been coated with ethylene glycol derivatives and have been shown to resist protein binding on a flat gold surface. Additionally gold nanoparticles coated with polyethylene glycol have been shown to be water soluble. However, the neutral glycols cannot react easily with biomolecules, and the monolayer thickness is not well defined, particularly with large polymer chains.

Foos et. al (*Chem. Mater.* (2002), 14, pg 2401-2408) have prepared a gold nanocluster coated with short chain ethylene glycol oligomers in a monolayer. However, the authors used a two-phase organic solvent system (as opposed to an aqueous/organic mixed solvent) for preparation and not all of the coated particles were found to be water-soluble.

Applicants have solved the deficiencies in the prior art by constructing a water soluble, metallic nanoparticle with a mixed monolayer, comprising a capture component and a shielding component with well defined thickness or length using a single phase organic/aqueous solvent system. The shielding component, (thiolated ethylene glycol short chain oligomers with well defined thickness or length), functions to minimize the non-specific interaction between nanoparticles and biological molecules, whereas the capture coating component, (e.g. tiopronin), serves as ligand to engage biological molecules specifically.

SUMMARY OF THE INVENTION

In one embodiment the invention provides a process for the preparation of a water soluble metallic nanoparticle coated with a mixed monolayer comprising:
  a) providing a water soluble metallic nanoparticle coated with monolayer of a capture coating component having an affinity for a capture moiety;
  b) mixing the coated nanoparticle of (a) with a shielding coating component having metal binding functionality in a mixed solvent; the mixed solvent comprising at least one substantially water miscible organic solvent and at least one aqueous solvent wherein the mixed solvent is at a pH of less than 7.0; wherein exchange occurs between the shielding coating component and the capture coating component to form a nanoparticle coated with a mixed monolayer; and
  c) optionally isolating the mixed monolayer coated metal nanoparticle of (b).

In an alternate embodiment the invention provides a process for the preparation of a water soluble metallic nanoparticle coated with a mixed monolayer comprising:
  a) providing;
    i) a metal salt
    ii) a shielding component having metal binding functionality;
    iii) a capture coating component having metal binding functionality and having an affinity for a capture moiety;
    iv) a suitable reducing agent; and
    v) a mixed solvent comprising at least one substantially water miscible organic solvent and at least one aqueous solvent wherein the mixed solvent is at a pH of less than 7.0;
  b) mixing elements (i)-(iv) in the mixed solvent of (v) to form a reaction mixture, wherein the final concentration of water in the reaction mixture is from about 9% to about 18% V/V, and wherein a mixed monolayer forms on the metallic nanoparticle; and
  c) optionally isolating the mixed monolayer coated metal nanoparticle of (b).

In a similar embodiment the invention provides a process for the synthesis of a water soluble metallic nanoparticle coated with a mixed monolayer comprising:
  a) providing a first reaction mixture comprising:
    (i) a metal salt
    (ii) a shielding component having metal binding functionality;
    (iii) a capture coating component having metal binding functionality and having an affinity for a capture moiety;
    (iv) an organic solvent;
  b) providing a second reaction mixture comprising a suitable reducing agent in an aqueous solvent; wherein the second reaction mixture is at a pH of less than 7.0; and
  c) mixing the first and second reaction mixtures wherein the final concentration of water in the mixture is from about 9% to about 18% V/V, and wherein a water soluble metallic nanoparticle coated with a mixed monolayer is formed.

In another preferred embodiment the invention provides a process for the preparation of a water soluble metallic nanoparticle coated with monolayer of a capture coating component comprising:
- a) mixing a metal salt with a capture coating component having an affinity for a capture moiety, the capture coating component comprising a metal binding functionality to form a first reaction mixture, wherein the first reaction mixture is at a pH of less than 7.0; and
- b) adding a suitable reducing agent to the first reaction mixture of (a) to form a second reaction mixture comprising metal nanoparticles coated with said capture coating component.

In another aspect the invention provides a process for the preparation of a water soluble gold nanoparticle coated with a mixed monolayer comprising:
- a) mixing a gold salt with tiopronin, the tiopronin comprising a SH functionality, together in a mixed solvent to form a first reaction mixture, wherein the first reaction mixture is at a pH of less than 7.0, and the mixed solvent is comprised of alcohol and water;
- b) adding $NaBH_4$ to the first reaction mixture of (a) to form a second reaction mixture comprising gold nanoparticles coated with said tiopronin;
- c) adding short chain ethylene glycol oligomers having an SH functionality wherein a mixed monolayer comprising tiopronin and the short chain ethylene glycol oligomers is formed on the gold particle and the nanoparticle is water soluble; and
- d) optionally isolating the mixed monolayer coated gold nanoparticle of (c).

Additionally the invention provides a water soluble metal nanoparticle coated with a mixed monolayer, the mixed monolayer comprising a shielding coating component consisting of ethylene glycol having metal binding functionality and a capture coating component having a binding functionality for a capture moiety.

Similarly the invention provides a process for immobilizing a capture moiety comprising contacting the water soluble metal nanoparticle of the invention with a capture moiety under conditions that permit the binding of the capture moiety to the capture coating component wherein the capture moiety is immobilized.

DETAILED DESCRIPTION OF THE INVENTION

The invention relates to nanoparticles coated with a mixed monolayer. The mixed monolayer is comprised of a shielding coating component and a capture coating component. The capture component acts to bind various capture moieties such as peptides or nucleic acids. The shielding component acts to shield the nanoparticle from non-specific binding of materials that are not capture moieties. The coated nanoparticles are typically metal based and are water soluble. The invention additionally relates to methods for the synthesis of the mixed monolayer coated nanoparticles.

The coated nanoparticles of the present invention are useful in the fabrication of nanodevices where uniform water soluble particles are needed as binding agents for the immobilization of, and attachment to, proteins and nucleic acids and other materials in a specific fashion. Additionally the coated nanoparticles of the invention may be used in of nanoscale electronic devices, multifunctional catalysts, chemical sensors, and many biological applications such as biosensors, biological assays.

The following definitions and abbreviations will be used herein for the interpretation of the claims and the specification:

"DMSO" is the abbreviation for dimethyl sulfoxide

"THF" is the abbreviation for tetrahydrofuran

"DMF" is the abbreviation for dimethylformamide

"GSH" refers to the chemical compound glutathione.

"TP" is the abbreviation for tiopronin

"Nanoparticles" are herein defined as metallic particles with an average particle diameter of between 1 and 100 nm. Preferably, the average particle diameter of the particles is between about 1 and 40 nm. As used herein, "particle size" and "particle diameter" have the same meaning. The metallic nanoparticles include, but are not limited to, particles of gold, silver, platinum, palladium, iridium, rhodium, osmium, iron, copper, cobalt, and alloys composed of these metals. An "alloy" is herein defined as a homogeneous mixture of two or more metals.

A "monolayer" refers to a layer of material coated on a nanoparticle that is the thickness of single molecule.

A "mixed monolayer" refers to a monolayer having at least two different molecular components.

A "capture moiety" refers to a substance that binds specifically to a capture coating component. Capture moieties may be any substance and typically are biopolymers such as peptides, proteins and nucleic acid fragments.

A "capture coating component" as used herein refers to a material capable of forming a monolayer on a nanoparticle that has an affinity for some ligand or capture moiety. The "capture" component makes up the lesser portion of a mixed monolayer and may comprise less than 50% of the monolayer.

A "shielding coating component" refers to a material capable of forming a monolayer on a nanoparticle that has the ability to prevent non-specific binding of substances that are not capture moieties. Shielding coating components may be comprised of a variety of materials where ethylene glycol is particularly suitable.

The term "entanglement molecular weight" as used in reference to the shielding component of the mixed monolayer means the minimum molecular weight beyond which the polymer molecules used as shielding component show entanglement. Methods of determining the entanglement molecular weight of a polymer are known, see for example Friedrich et al., Progress and Trends in Rheology V, Proceedings of the European Rheology Conference, 5th, Portoroz, Slovenia, Sep. 6-11, 1998 (1998), 387. Editor(s): Emri, I. Publisher: Steinkopff, Darmstadt, Germany.

The term "nano-structure" means tubes, rods, cylinders, bundles, wafers, disks, sheets, plates, planes, cones, slivers, granules, ellipsoids, wedges, polymeric fibers, natural fibers, and other such objects which have at least one characteristic dimension less than about 100 microns.

The terms "nano-rod" means a variety of nano-structures which may be either hollow or solid and may or may not have a circular corssectional shape. Nano-rods of the invention may include nanotubes, nanofibers, polymeric nanofibers, bundles and multiwalled structures.

The term "nanotube" refers to a hollow article having a narrow dimension (diameter) of about 1-200 nm and a long dimension (length), where the ratio of the long dimension to the narrow dimension, i.e., the aspect ratio, is at least 5. In general, the aspect ratio is between 10 and 2000.

By "nanoplanes" is meant surfaces which have one characteristic dimension less than 500 nanometer, for example a single or a dual layer of graphite or graphene sheets.

By "nanofibers" is meant natural or polymeric filaments which have a small dimension of less than 1000 nanometer.

The term "metal binding functionality" refers to a chemical group that effects attachment of a molecule to a metal surface. One non-limiting example of a metal binding functionality is the sulfhydral (—SH) functional group that effects the binding of materials to gold and other metals.

The term "mixed solvent" refers to a solvent comprising both an organic component and an aqueous component, wherein the organic component is substantially water miscible.

A "substantially water-miscible organic solvent" is herein defined as an organic solvent that dissolves completely in water up to a concentration of at least 80% by volume.

The term "Ligand-replacement method" refers to a method of coating a nanoparticle with a mixed monolayer where a first component of the mixed monolayer is coated on the nanoparticle and then elements of the first component are subsequently replaced with elements of a second component until a mixed monolayer is achieved.

The term "direct-synthesis method" refers to a method of coating a nanoparticle with a mixed monolayer where both components of the mixed monolayer are reacted in a single solution in the presence of the metal nanoparticle where a mixed monolayer is formed on the nanoparticle.

Coated Nanoparticles

The invention provides a water soluble metal nanoparticle coated with a mixed monolayer. The mixed monolayer comprises a shielding coating component and a capture coating component. The capture component has an affinity for a specific capture moiety and is affixed to the surface of the metal nanoparticle. The shielding component has the effect of blocking non-specific binding of materials that are not capture moieties to the capture component of the mixed monolayer.

Nanoparticles of the invention may be comprised of a variety of metals, including but not limited to gold, silver, platinum, palladium, iridium, rhodium, osmium, iron, copper, cobalt, and alloys composed of these metals. Preferred for use herein are nanoparticles comprised of gold. Typically un-coated nanoparticles of the invention range in diameter from bout 1 nm to about 100 nm, where from about 1 nm to about 40 nm is preferred. Methods of preparing metal nanoparticles are well known in the art (see for example Templeton, A. C. et al., *Acc. Chem. Res.* 2000, 33, 27-36) and are additionally available commercially from sources such as Sigma Chemical Company.

The nanoparticles of the invention are coated with a mixed monolayer having a capture component and a shielding component as part of the same monolayer. Typically the capture component comprises less than about 50% of the mixed monolayer where about 20%-40% is preferred. Conversely the shielding component forms the major component of the monolayer and comprises at least about 50% of the monolayer, where 60% to about 90% is preferred.

The capture component functions to bind various materials to the coated nanoparticle. It is preferred if the capture component has a specific affinity for a single capture moiety, although it is within the scope of the present invention to include a capture component that has multiple binding sites for a variety of different capture moieties. Typical capture moieties of the invention include for example, biopolymers such as peptides, proteins, nucleic acid fragments, and collagen, as well as nanomaterials useful in the assembly and synthesis of nanodevices such as for example various nano-structures (nano-rods, nano-tubes, nano-planes and nano-fibers as defined herein). The capture component may be functionalized with various chemical groups that allow for binding to a capture moiety. Non-limiting examples of such chemical reactive groups include those selected from the group consisting of: —NH$_2$, —COOH, —CHO—, —OH, —X (Cl, Br, I), succinimide, and epoxy groups. Preferred examples of suitable capture components are tiopronin and GSH. Tiopronin (abbreviated TP), is N-2-mercaptopropionyl-glycine is particularly suitable as a capture component because of the presence of exposed carboxy groups (as illustrated below) which serves as a convenient binding site for biomolecules.

The shielding component of the mixed monolayer serves to block the binding of non-capture moiety materials to the coated nanoparticle and permits the nanoparticle to be used to bind, isolate or immobilize specific capture moieties. The principal requirement of the shielding component is that it not bind the capture moiety, and typically will be an uncharged, water soluble molecule of well defined length. Polymers of excessive length may have the effect of blocking the binding sites on the capture component and thus polymer length must be controlled. Suitable shielding components will include but are not limited to short chain ethylene glycol oligomers, ethylene glycol methacrylate, sugars, crown ethers, and acrylamide, where the short chain ethylene glycol oligomers are preferred.

Figure 1:
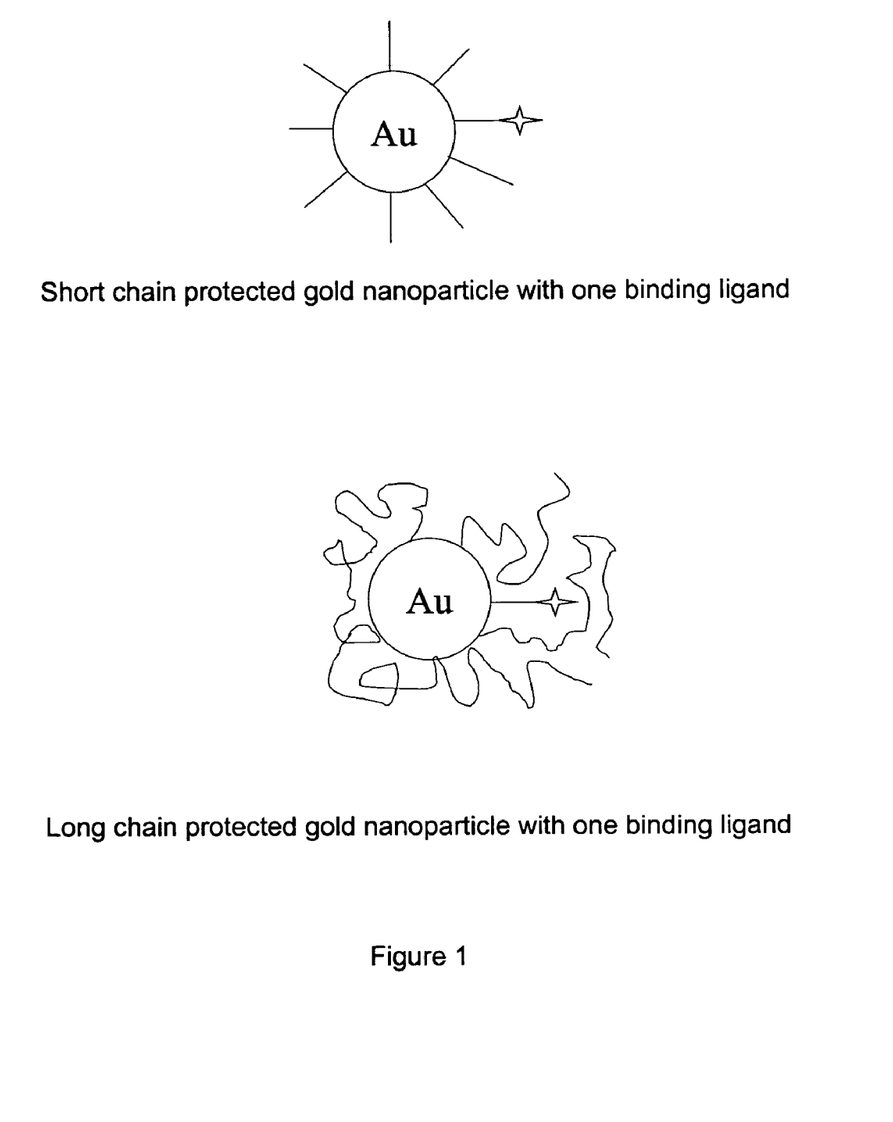
FIG. 1 is an illustration of a short chain protected gold nanoparticle with one binding ligand and a long chain protected gold nanoparticle with one binding ligand.

The shielding component will be functionalized to bind to the surface of the metal nanoparticle. A common method of conveying metal binding functionality to a material is the addition of a sulfhydral group as illustrated below for two of the preferred short chain ethylene glycol oligomers:

Although any short chain ethylene glycol oligomers are suitable it is generally preferred if they are limited in size such that they are less than the entanglement molecular weight of the oligomer. While not meaning to suggest a mechanism for this preference, it is believed that short chain shielding components are more suitable as opposed to long polymer chains to avoid blocking the binding sites of the capture component, as illustrated in FIG. 1. It is reasonable to expect that short chain shielding components will allow the capture moiety binding sites on the capture component to be accessible to the capture moiety. Longer chain major components may block the capture moiety binding functionality, preventing any binding from occurring.

Synthesis of Coated Nanoparticles

The present invention provides methods of synthesizing coated nanoparticles of the invention that are new. Two principal methods are practiced herein and are identified as a ligand-replacement method and a direct synthesis method. The two methods differ principally in the order of the addition of components, and will be described in greater detail below.

Ligand-Replacement

The ligand-replacement method proceeds with the coating of a metal nanoparticle with a first component of the mixed monolayer, followed by exposure of the coated particle to a second component. Under the appropriate reaction conditions, elements of the first component are replaced by elements of the second component such that a mixed monolayer is formed. The ligand-replacement method comprises the following process steps:

a) providing a water soluble metallic nanoparticle coated with monolayer of a capture coating component having an affinity for a capture moiety; and b) mixing the coated nanoparticle of (a) with a shielding coating component in a mixed solvent, the shielding component having metal binding functionality; the mixed solvent comprising at least one substantially water miscible organic solvent and at least one aqueous solvent wherein the mixed solvent is at a pH of less than 7.0; wherein exchange occurs between the shielding coating component and the capture coating component to form a nanoparticle coated with a mixed monolayer.

Optionally the mixed monolayer coated metal nanoparticle of may be isolated from solution by standard methods such as filtration, centrifugation, or distillation.

Of particular importance in the ligand-replacement method for the preparation of the mixed monolayer is the use of a mixed solvent at an acidic pH. The mixed solvent comprises an aqueous portion and an organic portion where the organic portion is substantially miscible in water. Suitable organic solvents include, but are not limited to, C1-C6 alkanols (e.g. methanol, ethanol, isopropanol), dimethyl sulfoxide, tetrahydrofuran, dimethylformamide, Dioxane, and acetone. Suitable solvents also include mixtures of organic solvents that are completely miscible with each other and that result in a mixture which is a substantially water-miscible organic solvent. Examples of multi-component organic solvents include, but are not limited to, ethyl acetate and methanol; ethyl acetate and ethanol; ethyl acetate and isopropanol; ethyl acetate and acetone; ethyl acetate, dimethylformamide and dimethyl sulfoxide; and ethyl acetate, tetrahydrofuran, and dioxane. The preferred organic solvent is methanol or ethanol.

The aqueous portion of the mixed solvent may simply be water, however it is generally an acid such as acetic acid since it is preferable if the reaction take place in an acid environment, generally at a pH of less than about 7.0 where a pH of less than about 5.5 is preferred.

The ligand replacement method relies on providing a metallic nanoparticle coated with a monolayer. Methods of synthesizing a nanoparticle coated with a single monolayer are known. For example, Templeton et al. (*Langmuir* 15:66-76 (1999)), herein incorporated by reference, describe a method for the preparation of, charged, water-soluble gold nanoparticles protected by tiopronin or coenzyme A monolayers. To prepare the tiopronin-protected gold nanoparticles, tetrachloroauric acid and N-(2-mercaptopropionyl)glycine (tiopronin) were codissolved in a mixture of methanol and acetic acid. Sodium borohydride was added with rapid stirring. The coenzyme A protected gold nanoparticles were prepared in a similar manner by substituting coenzyme A for tiopronin in the reaction. In addition to gold, other metals may be used. For example Heath et al. in U.S. Pat. No. 6,103,868, describe the coating of gold, silver, platinum, palladium, cobalt and nickel with a solution of an organic surface passivant that had a functional group such as a thiol, phosphine, disulfide, amine, oxide, or amide. Chen et al. (*Colloids and Surfaces A* 169:107-116 (2000)), herein incorporated by reference describes and alternate method involving the preparation of nanoparticles in an ethanol-water mixture by the reduction of chloroplatinic acid by ethanol in the presence of poly(N-vinylisobutyramide). Other methods are also described, see for example Hagemeyer et al. in U.S. Pat. No. 6,074,979; Wuelfing et al. (*J. Am. Chem. Soc.* 120:12696-12697 (1998)); Chan et al. (*Science* 281:2016-2018 (1998)); Mitchell et al. (*J. Am. Chem. Soc.* 121:8122-8123 (1999)); and Napper (*J. Colloid. Interface. Sci* 58:390-407 (1977)).

Accordingly a preferred method of synthesis of a nanoparticle coated with the capture component for use in the present invention involves the following process steps:

a) mixing a metal salt with a capture coating component having an affinity for a capture moiety, the capture coating component comprising a metal binding functionality to form a first reaction mixture, wherein the first reaction mixture is at a pH of less than 7.0; and b) adding a suitable reducing agent to the first reaction mixture of (a) to form a second reaction mixture comprising metal nanoparticles coated with said capture coating component.

When using the above, or similar method for the preparation of the nanoparticle coated with a single monolayer it is useful to begin with a metal salt. Suitable metal salts include, but are not limited to, any salts of the metals, gold, silver, platinum, palladium, iridium, rhodium, osmium, iron, copper, cobalt, and alloys composed of these metals. Particularly suitable salts include $HAuCl_4$, $AgNO_3$, $Cu(CH_3CO_2)_2$, $Cu(NO_3)_2$, $HPtCl_6$, and $K_2PdCl_4$.

A reducing agent is needed for the bonding of the metal binding functionalized capture or shielding component to the surface of the metal nanoparticle. Metal binding functionality is generally conveyed to the capture or shielding coating component by the addition of various reactive groups that will bind metal surfaces after reduction. A typical reactive group of this sort is the sulfhydral (—SH) group which can be used to derivatize many suitable capture coating components. Typical reducing agents are those that interact with the metal-binding functional group on the capture component. Suitable reducing agents where the metal binding functional group is —SH are $NaBH_4$, lithium triethylborohydride and hydrogen peroxide.

Direct-Synthesis

In contrast to the two step ligand-replacement method, it is also possible to synthesize the mixed monolayer coated nanoparticles of the invention by a single step, direct synthesis method. This method is useful where the shielding component is comprised of ethylene glycol. The direct synthesis method proceeds by the following process steps:

a) providing;
  i) a metallic nanoparticle
  ii) an ethylene glycol component having metal binding functionality;
  iii) a capture coating component having metal binding functionality and having an affinity for a capture moiety;
  iv) a suitable reducing agent; and
  v) a mixed solvent comprising at least one substantially water miscible organic solvent and at least one aqueous solvent wherein the mixed solvent is at a pH of less than 7.0; and
b) mixing elements (i)-(iv) in the mixed solvent of (v) to form a reaction mixture, wherein the final concentration of water in the reaction mixture is from about 9% to about 18% V/V, and wherein a mixed monolayer forms on the metallic nanoparticle.

Optionally the coated nanoparticles may be isolated according to any means known in the art.

Alternatively the direct synthesis method may employ a series of steps that initially separate the components of the mixed solvent. Good results have been achieved when the metal salt, shielding component, capture component are dissolved in an organic solvent and then mixed with a reducing agent dissolved in water. The final solution should be at pH of less than 7.0, and it is preferred if the final concentration of water in the mixture is from about 9% to about 18% V/V. Accordingly the invention provides a process for the synthesis of a water soluble metallic nanoparticle coated with a mixed monolayer comprising:

a) providing a first reaction mixture comprising:
  (i) a metal salt
  (ii) a shielding component having metal binding functionality;
  (iii) a capture coating component having metal binding functionality and having an affinity for a capture moiety;
  (iv) an organic solvent;
b) providing a second reaction mixture comprising a suitable reducing agent in an aqueous solvent; wherein the second reaction mixture is at a pH of less than 7.0; and
c) mixing the first and second reaction mixtures wherein the final concentration of water in the mixture is from about 9% to about 18% V/V, and wherein a water soluble metallic nanoparticle coated with a mixed monolayer is formed.

The direct synthesis method offers the advantage of single reaction step, however it is essential that the amount of water in the reaction mixture be controlled. For example, final water content of the reaction should be from about 5% to about 20% (V/V) where from about 9% to about 18% (V/V) is preferred. In the direct synthesis method the solubility of the nanoparticles is sensitive to the concentration of water and fluctuations in the water concentration may result in the nanoparticles precipitating out of solution.

The average size of the resulting nanoparticles synthesized by either method may be controlled by changing the molar ratio of the metal salt and the capture coating component, as described in "Water-Soluble, Isolable Gold Clusters Protected by Tiopronin and Coenzyme A Monolayers", A. C. Templeton, S. Chen, S. M. Gross, and R. W. Murray, Langmuir, 1999, 15, pp 66-76.

Either of the above described processes may be performed at room temperature, although higher or lower temperatures can also be utilized.

Capture

The coated nanoparticles of the present invention may be used to capture or immobilize a variety of materials in a variety of formats. For example, it is contemplated that a nanoparticle may be engineered to specifically bind a protein ligand which may in turn have an affinity for nucleic acids of a specific sequence. Using this format consecutive nanoparticles could be aligned on a single nucleic acid template to form a nano-wire for electric conduction.

Alternatively nanoparticles of the invention could be functionalized to have an affinity for specific proteins or nucleic acids. Free proteins or nucleic acids could be captured on the surfaces of the nanoparticles and subsequently purified by the use of electrophoresis, or by the application of a magnetic or electromagnetic field.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Materials and Methods

Unless otherwise specified, all the reagents were purchased from Aldrich Chemicals (Milwaukee, Wis.) and used without further purification.

The meaning of abbreviations is as follows: "h" means hour(s), "min" means minute(s), "sec" means second(s), "d" means day(s), "mL" means milliliters, "L" means liters.

Example 1

Synthesis of diethylene glycol thiol (EG2-SH)

1-Bromo-2-(2-methoxyethoxy)ethane (90%, 10.0 g) and urea (99%, 8.3 g) were added into a 250 mL dried round bottom flask. Then 80 mL of ethanol (99.9%) was added into the flask. The mixture was refluxed for 6 hours. After the mixture was cooled down to room temperature, EtOH was removed by rotary evaporation. Then 150 g of 20% NaOH was added and refluxed for 3 hours. The mixture was cooled down to the room temperature and poured to a 500 mL beaker. 15% HCl (prepared from the concentrated HCl) was slowly added into the mixture with stirring until the pH reached 2. The mixture was extracted 4 times with 200 mL of ether. Liquid in ether phase was collected in a 1000 mL beaker and the ether phase was extracted with 200 mL D.I. water to further remove the salt and other impurities. The ether was removed by rotary evaporation and the crude product was distilled at 41-42° C. under 1.2 mm Hg pressure. The final product was colorless with a typical thiol odor, and weighed 6.0 g, giving a yield of 57%. The structure was confirmed by NMR measurements. $^1$H NMR (500 MHz, CDCl$_3$) δ: 1.60-1.65 (t, 1H), 2.70-2.80 (m, 2H), 3.45 (s, 3H), 3.55-3.75 (m, 6H).

Example 2

Synthesis of tetraethylene glycol thiol (EG4-SH)

Phosphorous tribromide (9.0 g, 0.033 mole) (PBr$_3$, 99%) was slowly added to a stirred mixture of 10.0 g (0.048 mole) of tetra(ethylene glycol) monomethyl ether (98%, Alfa Aesar, Ward Hill, Mass.) and 2 g of pyridine at 0° C. The resulting mixture was stirred at room temperature for 16 hours. 10 mL of D.I. water was added to the reacted mixture. The mixture was extracted 3 times with 40 mL of carbon tetrachloride. The combined organic extracts were rinsed successively with 25 mL of 10% sodium carbonate aqueous solution, 5% sulfuric acid, and D.I. water. The organic phase was further dried over anhydrous magnesium sulfate and the solvent was removed by rotary evaporation. The crude product was used for the further synthesis of tetraethylene glycol thiol. The procedures were the same as that for the synthesis of diethylene glycol thiol. The yield was ~20%, due to the fact that EG4-SH is very soluble in water and a lot of product was lost at the ether extraction step. The color of EG4-SH was pale yellowish with a smell characteristic of thiol compounds. The structure was confirmed by NMR spectra. $^1$H NMR (500 MHz, CDCl3) δ: 4.46 (s, 1H), 3.37 (s, 3H), 3.53-3.59 (t, 2H), 3.59-3.66 (m, 14H).

Example 3

Synthesis of tiopronin Monolayer-Protected Gold Nanoparticles [Au-(TP)$_n$] with Average Diameter of 3.5 nm In a typical reaction, 60 mL MeOH (HPLC grade) and 10 mL acetic acid (HPLC grade) were mixed in a 250 mL Erlenmeyer flask by stirring for 2-5 minutes. Then, 0.37 g (1.0 mmol) tetrachloroauric acid (HAuCl$_4$.xH$_2$O) (99.99%) and 16.32 mg (0.1 mmol) N-(2-mercaptopropionyl)glycine (tiopronin, 99%) were added to the above mixed solvents and dissolved by stirring for 5 minutes, which gave a clear and yellow solution. Dissolve 0.6 g (16 mmol) sodium borohydride (NaBH$_4$, 99%) in 30 g Nanopure® water. The NaBH$_4$ solution was drop-wise added into the above solution with rapid stirring. With the first drop of NaBH$_4$ was added, the HAuCl$_4$ solution was immediately turned to dark brown from yellow. It was noticed that this reaction is exothermic. The heat generated in the reaction would make the solution warm for ~15 min. During the reaction, the pH of the solution changed from 1.2 to ~5.0. Rapid stirring was kept for two hours. The tiopronin protected gold nanoparticles were soluble in water. When diluted, it became purple and clear.

The average size of the nanoparticles could be tuned by changing the molar ratio of [HAuCl$_4$] and [tiopronin]. With the ratio increasing, the average particle size also increases.

Example 4

Synthesis of Di(ethylene glycol) Protected Nanoparticles by Replacement Reactions

A typical synthesis for Au-EG2 was to mix 5 mL aqueous tiopronin monolayer protected gold nanoparticle (20 mg, ~5×10$^{-3}$ mmole of tiopronin) with 0.75 mL EtOH containing 30 mg EG2-SH (0.22 mmol, ~40× of tiopronin on gold nanoparticle surface) in a 25 mL round bottom flask. After the mixture was stirred for 24 hours at room temperature, it was transferred to a filter sample vial and centrifuged to collect gold nanoparticles. Then the sample was washed twice with Nanopure® water to get purified EG2-SH protected gold nanoparticles (Au-EG2). Au-EG2 nanoparticles can be easily re-dissolved in water.

A typical synthesis for Au-EG4 was to mix 20 mL aqueous tiopronin monolayer protected gold nanoparticles (3 nm particle size, 0.185 g, ~0.05 mmole of tiopronin) was mixed with 6 mL EG4-SH ethanol solution (448 mg of EG4-SH, 2.0 mole, ~40×) in a 50 mL round bottom flask and stirred for 24 hours at room temperature. Au-EG4 nanoparticle was purified either by dialysis or centrifuging. For dialysis, Au-EG4 solution was transferred to the membrane tubing (Spectrum, MWCO 3,500). The membrane filled with Au-EG4 was stirred in 2 L Nanopure® water for 24 hours with the water changed every 4 hours. Au-EG4 nanoparticles could also be purified by centrifugation. Au-EG4 reaction mixture was transferred to a filter sample vial and centrifuged to collect gold nanoparticles. Then the sample was washed twice with Nanopure® water to get purified EG4 protected gold nanoparticles (Au-EG4). Au-EG4 nanoparticles can be easily re-dissolved in water.

The Au-TP, Au-EG2 and Au-EG4 particles were removed from the test tube after drying, and mounted directly into the ToF-SIMS. The samples were analyzed using a Physical Electronics Model 7200 Time of Flight Secondary Ion Mass Spectrometer. The surface was irradiated with a 8 KeV Cs+ ion beam rastered over a 200 micron×200 micron area. Both positive and negative secondary ions were collected over a mass range of 5-1500. ToF-SIMS is very surface specific being sensitive to the outermost 10 Å of the surface and was used to probe the surface structures of the nanoparticles. Both positive and negative secondary ions were collected and reviewed. The surface structures of Au-TP, Au-EG2, and Au-EG4 are shown below.

Designation: Au-TP: Mass of Thiol Attachment (162)

Designation: Au-EG2: Mass of Thiol Attachment (135)

Designation: Au-EG4: Mass of Thiol Attachment (223)

All surfaces analyzed showed a clear Au$_x^-$ (x=1-6) series as well as AuS, Au$_2$S, Au$_2$S$_2$, Au$_3$S, Au$_3$S$_2$, Au$_3$S$_3$ negative ions. These fragments confirmed the Au—S bonding for all three nanoparticles.

Au-TP Particles:

The spectra for Au-TP showed a strong negative secondary ion signal for the TP ligand at mass 162. Additional negative ion peaks at mass 359 Au(TP)$^-$ and 556 Au$_2$(TP)$^-$ were also clearly observed. It should be cautioned that the presence of a Au$^+$ ligand ion may arise from two sources: the formation of a cluster ion after ion bombardment (a SIMS effect); or the ionization of a Au ligand complex existing on the surface prior to analysis. Ion assigned as CN at mass 26 and CNO at mass 42 respectively were observed in the negative ion spectrum. This is a typical signature for amides and is used as an indication (ratio to Au—) of the relative amount of TP present on the surface of the Au particles. The ratio of mass 42/197 (CNO/Au) for each of the three samples is shown below.

| Sample | 42/197 (−) Ion Ratio |
|---|---|
| Au-TP | 0.365 |
| Au-EG2 | 0.010 |
| Au-EG4 | 0.025 |

The ratio data shows that tiopronin present on the gold nanoparticles was significantly reduced after replacement reactions by EG2-SH and EG4-SH, even though the quantitative ratio of tiopronin and $EG_n$-SH (n=2 and 4) on the Au nanoparticle surface could not be derived from data.

Au-EG2 Particles: In addition to the Au and $Au_xS_y$ clusters described above, the presence of negative ion peaks at 332 $Au(EG2)^-$ and 529 $Au_2(EG2)^-$ ions were distinguishing features of the surface of the Au-EG2 particles. Sodium was significantly reduced on these surfaces relative to Au-TP sample. The negative ion spectrum showed high $PO_3^-$ and $SO_3^-$, indicating these anions were introduced with buffer solutions in this system.

Au-EG4 Particles: The negative ion spectrum for the Au-EG4 particles was similar to the Au-EG2 surface with Au cluster ions, Au sulfide ion series, the presence of $PO_3^-$ and $SO_3^-$. Negative ion peaks at 420 $Au(EG4)^-$ and 617 $Au(EG4)^-$ were also observed.

Example 5

Metal Ion Chelating with Monolayer Protected Nanoparticles

A drop of 1M $CaCl_2$ solution was added to 0.2 mL tiopronin protected nanoparticles (Au-TP), Au-EG2 and Au-EG4 aqueous solutions, separately. Au-TP solution immediately turned to blue upon addition of the $Ca^{+2}$ and the particle agglomeration was formed via chelation of $Ca^{+2}$ ions by —COOH groups from different particles, as shown below. When a drop of EDTA solution was added, the color of the agglomerated solution changed back to red purple, the color of the original Au-TP, indicating that the agglomerated solution became soluble again. Upon addition of the $CaCl_2$ to Au-EG2 and Au-EG4 aqueous solution, no color change or precipitation was observed, indicating that the Au-EG2 and Au-EG4 nanoparticles have negligible tiopronin molecules on the surfaces. This data agrees with the data from the Tof-SIMS that the majority of tiopronin molecules are replaced by EG2-SH and EG4-SH, forming EG2 and EG4 protected nanoparticles.

Example 6

Gel Electrophoresis Analysis of Protein Binding

Protein binding to Au nanoparticles can be conveniently monitored by gel electrophoresis, since protein-nanoparticle complex are expected to migrate differently than the free Au particles. Protein binding reactions were done by mixing 1 µl of ~1 µM Au particles with certain amount of protein in 10 µL of sodium phosphate buffer (50 mM, pH 7.3). After incubation at room temperature for 10 min, the entire reaction mixture was loaded on 1% agarose gel. Gel electrophoresis was run in 1×TBE buffer (Tris-borate-EDTA) at 90V constant voltage for 20 min. Gel pictures were taken by directly scanning the gel on a HP ScanJet 6300C.

Figure 2:
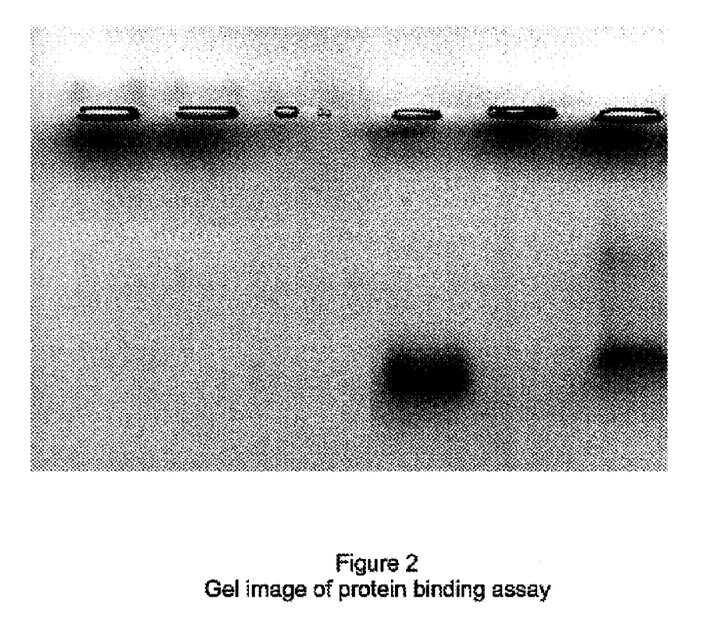
FIG. 2 is a gel electrophoresis image of protein binding assay to Au-EG4 and Au-Tp particles.

Results are shown in FIG. 2. Lane 1: 1 µL of Au-EG4 at ~1 µM in 10 µL of sodium phosphate buffer (50 mM, pH 7.3), Lane 2 and 3 are the same amount of Au particles mixed with 4 µg of lysozme, streptavidin in 10 µL of sodium phosphate buffer (50 mM, pH 7.3), respectively. Lanes 4 to 6 are similar to Lane 1-3, except that Au-Tp particles were used.

When Au-Tp particles were mixed with streptavidin, and lysozyme, different degrees of non-specific binding were observed, as indicated by the band-shifts. When the same experiment was done with Au-EG4 particles, no change was observed. The most dramatic contrast was provided by the reaction between Au-Tp particles and lysozyme. Addition of lysozyme into the Au-Tp particle solution causes an immediate color change from pinkish red to blue, indicating that Au particles form aggregates, presumably because the positively changed lysozyme (pl=11) molecules cross-link negatively charged Au-Tp particles. However, when lysozyme was mixed with Au-EG4 solutions, no color change was observed.

Example 7

Ion Exchange Chromatography Analysis of Protein Binding to Au-EG4

Figure 3:
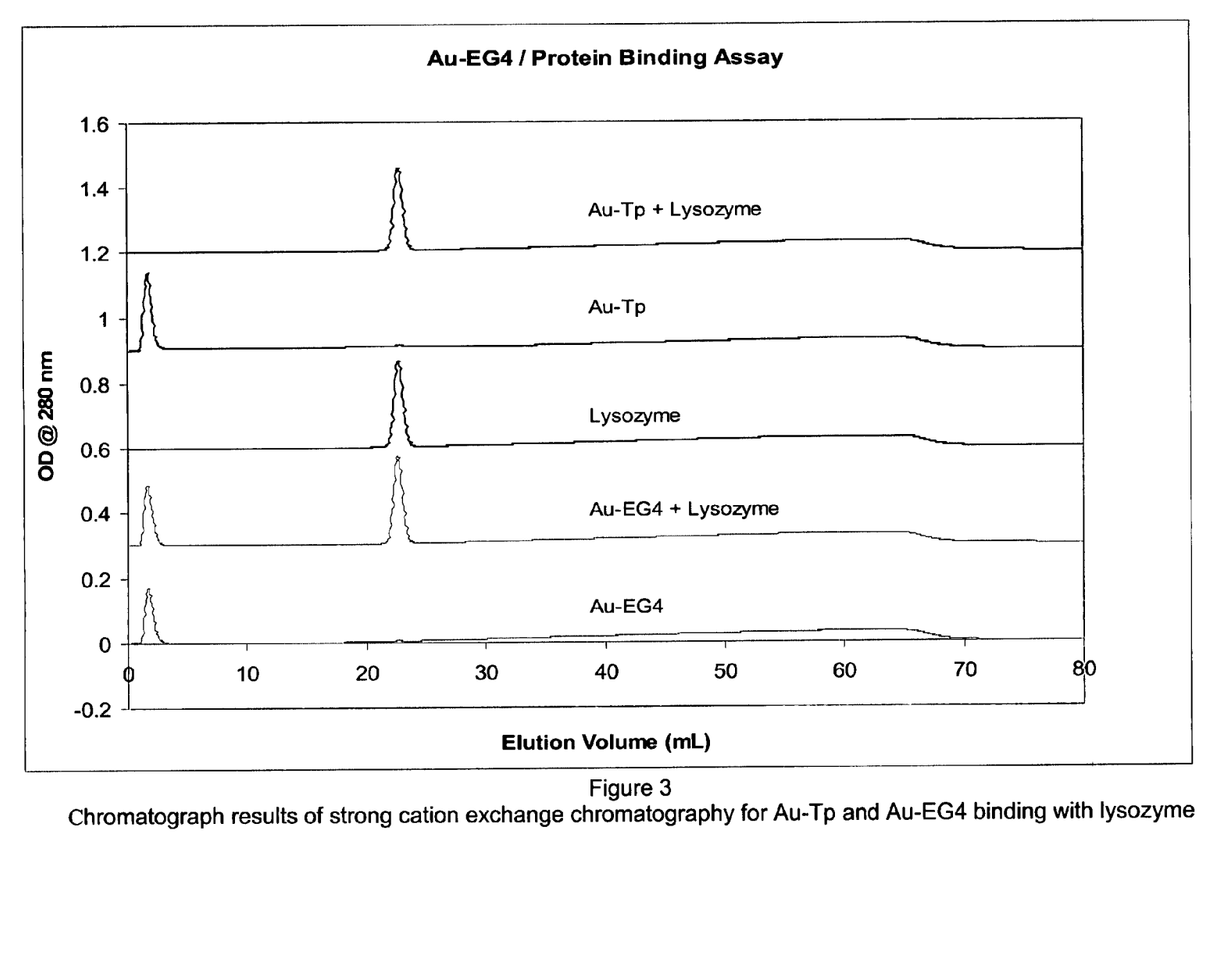
FIG. 3 is a chromatograph showing the results of strong cation exchange chromatography for Au-Tp and Au-EG4 binding with lysozyme.

Ion exchange chromatography analysis of protein binding to Au-EG4 and Au-tiopronin particles was carried out using BioCAD/SPRINT HPLC system (PerSeptive Biosystems, Framingham, Mass.) with cation exchange column HS20 (PerSeptive Biosystems). In all cases, 0.1M MES (2-(N-morpholino)ethanesulfonic acid) buffer pH 7 with 0 to 2 M NaSCN salt gradient were used, with a flow rate of 10 mL/min. In a typical run, 0.3 mL of either Au-EG4 or Au-Tp (concentration: ~2 uM) in $NaH_2PO_4/K_2HPO_4$ buffer (pH=7.3) was mixed with an equal volume of 1 mg/ml protein or the phosphate buffer, incubated at room temperature for 2 hr. The reaction mixture was centrifuged at 13000 rpm in an Eppendorf 5415C for 10 min, loaded on to the column, and then eluted with 0 to 2 M NaSCN salt gradient. The results are shown in FIG. 3. Addition of lysozyme into Au-Tp particle solution caused an immediate color change from pinkish red to blue, indicating that Au particles form aggregates, presumably because the highly positively changed lysozyme (pI=11) molecules cross-link negatively charged Au-Tp particles. Centrifugation of the Au-Tp/lysozyme reaction mixture resulted in a clear supernatant, indicating that no soluble Au-Tp particles remained in the supernatant. The cation exchange column chromatography showed that only lysozyme proteins were present in the supernatant, as shown in FIG. 3. However, when lysozyme was mixed with Au-EG4 solutions, we observed no color change at all. Centrifugation of the Au-EG4/lysozyme reaction yielded no change of the solution. The reaction mixture was eluted from the HS20 cation exchange column as two separate species corresponding to lysozyme and Au-EG4 particles. This result indicates that there is no binding reaction occurring between Au-EG4 and lysozyme protein. Also tested were cytochrome C, ribonuclease A and myoglobin. In all cases no binding was observed between Au-EG4 the tested proteins, but varying degree of binding between Au-Tp and those proteins was seen.

Figure 4:
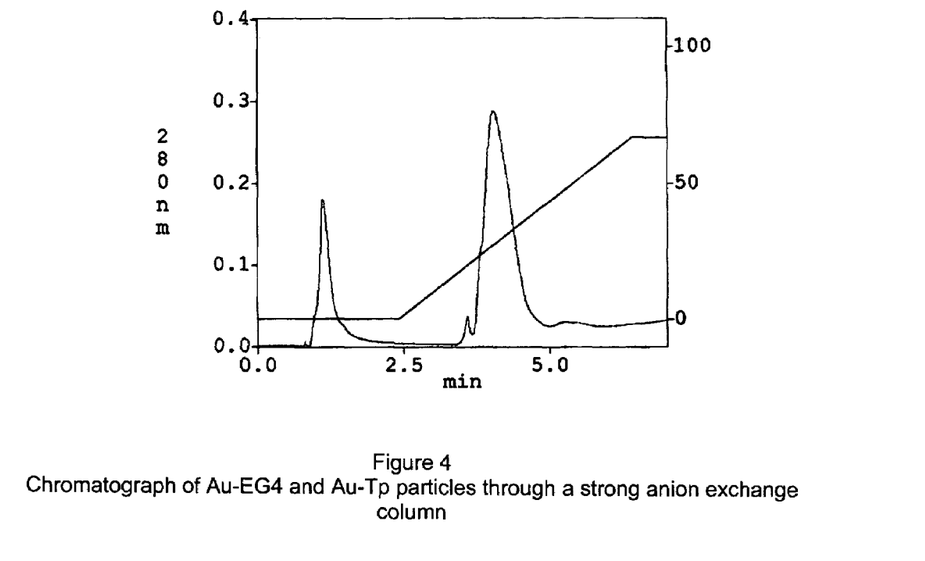
FIG. 4 is a chromatograph of Au-EG4 and Au-Tp particles through a strong anion exchange column.

Also tested were Au-EG4 particles on the anion exchange column HQ20 (PerSeptive Biosystems) (shown in FIG. 4). In this example, 1 mL of a Au-EG4 and Au-Tp mixture (~1:5) at a concentration of ~1 μM was loaded onto the HQ20 column and eluted with 0.1 M MES buffer at pH7 and a salt gradient from 0 to 2 M NaSCN. The $1^{st}$ peak corresponds to Au-EG4 and the $2^{nd}$ peak is from Au-Tp. Since Au-EG4 nanoparticles were eluted at the void volume from both cation and anion exchange columns, this indicates that the surface of Au-EG4 particles is charge neutral and does not bind to either column. This is consistent with the results of Au-EG4 particles' migration in agarose gel.

Example 8

Synthesis of Tetraethylene Glycol Monolayer-Protected Gold Nanoparticles (Au-EG4) with Average Diameter of 3.0 nm In a typical reaction, 30 mL MeOH (HPLC grade) and 5.0 mL acetic acid (HPLC grade) were mixed in a 150 mL Erlenmeyer flask by stirring for 2-5 minutes. Then, 0.0885 g (0.23 mmol) tetrachloroauric acid ($HAuCl_4.xH_2O$) (99.99%) and 22.4 mg (0.1 mmol) tetraethylene glycol thiol (EG4-SH) added to the above mixed solvents and dissolved by stirring for 5 minutes, which gave a clear and yellow solution. Next 0.075 g (2.0 mmol) sodium borohydride ($NaBH_4$, 99%) was dissolved in 5.0 mL Nanopure® water. The $NaBH_4$ solution was drop-wise added into the above solution with rapid stirring. With the first drop of $NaBH_4$ was added, the $HAuCl_4$ solution was immediately turned to dark brown from yellow. It was noticed that this reaction is exothermic. The heat generated in the reaction would make the solution warm for ~15 min. During the reaction, the pH of the solution changed from 1.2 to ~5.0. Rapid stirring was continued for two hours. The tetraethylene glycol protected gold nanoparticles are soluble in water. When diluted, it became red purple and clear.

The average size of the nanoparticles could be tuned by changing the molar ratio of $HAuCl_4$ and EG4-SH. With the increasing ratio, the average particle size also increases.

Example 9

Synthesis of Diethylene Glycol Monolayer-Protected Gold Nanoparticles (Au-EG2) with Average Diameter of 3.0 nm In a typical reaction, 30 mL MeOH (HPLC grade) and 5.0 mL acetic acid (HPLC grade) were mixed in a 150 mL Erlenmeyer flask by stirring for 2-5 minutes. Then, 0.0885 g (0.23 mmol) tetrachloroauric acid ($HAuCl_4.xH_2O$) (99.99%) and 13.6 mg (0.1 mmol) tetraethylene glycol thiol (EG4-SH) were added to the above mixed solvents and dissolved by stirring for 5 minutes, which gave a clear and yellow solution. Next 0.075 g (2.0 mmol) sodium borohydride ($NaBH_4$, 99%) was dissolved in 5.0 mL Nanopure® water. The $NaBH_4$ solution was drop-wise added into the above solution with rapid stirring. With the first drop of $NaBH_4$ was added, the $HAuCl_4$ solution was immediately turned to dark brown from yellow. It was noticed that this reaction is exothermic. The heat generated in the reaction would make the solution warm for ~15 min. During the reaction, the pH of the solution changed from 1.2 to ~5.0. Rapid stirring was continued for two hours. The diethylene glycol protected gold nanoparticles are soluble in water. When diluted, it became red purple and clear. The average size of the nanoparticles could be tuned by changing the molar ratio of $HAuCl_4$ and EG2-SH. With the increasing ratio, the average particle size also increases.

Example 10

Synthesis of Tetraethylene Glycol and Tiopronin Monolayer Protected Gold Nanoparticles (Au-EG4) with Average Diameter of 3.0 nm In a typical reaction, 30 mL MeOH (HPLC grade) and 5.0 mL acetic acid (HPLC grade) were mixed in a 150 mL Erlenmeyer flask by stirring for 2-5 minutes. Then, 0.0885 g (0.23 mmol) tetrachloroauric acid ($HAuCl_4.xH_2O$) (99.99%), 22.4 mg (0.1 mmol) tetraethylene glycol thiol (EG4-SH), and 1.63 mg of tiopronin (0.01 mmol) were added to the above mixed solvents and dissolved by stirring for 5 minutes, which gave a clear and yellow solution. Next 0.075 g (2.0 mmol) sodium borohydride ($NaBH_4$, 99%) was dissolved in 5.0 mL Nanopure® water. The $NaBH_4$ solution was drop-wise added into the above solution with rapid stirring. With the first drop of $NaBH_4$ was added, the $HAuCl_4$ solution was immediately turned to dark brown from yellow. It was noticed that this reaction is exothermic. The heat generated in the reaction would make the solution warm for ~15 min. During the reaction, the pH of the solution changed from 1.2 to ~5.0. Rapid stirring was continued for two hours. The tetraethylene glycol protected gold nanoparticles were soluble in water. When diluted, it became red purple and clear. The average size of the nanoparticles could be tuned by changing the molar ratio of $HAuCl_4$ and (EG4-SH+Tiopronin). With the increasing ratio, the average particle size also increases.

Example 11

Synthesis of Diethylene Glycol and Tiopronin Monolayer Protected Gold Nanoparticles (Au-EG2) with Average Diameter of 3.0 nm In a typical reaction, 30 mL MeOH (HPLC grade) and 5.0 mL acetic acid (HPLC grade) were mixed in a 150 mL Erlenmeyer flask by stirring for 2-5 minutes. Then, 0.0885 g (0.23 mmol) tetrachloroauric acid ($HAuCl_4.xH_2O$) (99.99%), 13.6 mg (0.1 mmol) diethylene glycol thiol (EG4-SH), and 1.63 mg of tiopronin (0.01 mmol) were added to the above mixed solvents and dissolved by stirring for 5 minutes, which gave a clear and yellow solution. Next 0.075 g (2.0 mmol) sodium borohydride ($NaBH_4$, 99%) was dissolved in 5.0 mL Nanopure® water. The $NaBH_4$ solution was drop-wise added into the above solution with rapid stirring. With the first drop of $NaBH_4$ was added, the $HAuCl_4$ solution was immediately turned to dark brown from yellow. It was noticed that this reaction is exothermic. The heat generated in the reaction would make the solution warm for ~15 min. During the reaction, the pH of the solution changed from 1.2 to ~5.0. Rapid stirring was continued for two hours. The tetraethylene glycol protected gold nanoparticles are soluble in water. When diluted, it became red purple and clear. The average size of the nanoparticles could be tuned by changing the molar ratio of $HAuCl_4$ and (EG2-SH+Tiopronin). With the increasing ratio, the average particle size also increases.

Example 12

NMR Analysis of Au—S-EG4 Nanoparticles $^1$H NMR spectra were recorded for free $EG_4$-SH and Au—S-$EG_4$ nanoparticles prepared as in Example 4. $^1$H NMR spectrum of free $EG_4$-SH was recorded with a Bruker 500 MHz at room temperature in $CCl_3D$. The peaks were labeled with the spectrum. The $^1$H NMR spectrum of Au—S-$EG_4$ nanoparticle was recorded with a Varian Inova 400 MHz at room temperature in DMSO-$d_6$. The sample was run with 1 pulse experiment using 900 pulse with 20 seconds delay. The baseline was flattened by using a spline baseline corrector. δ: 1.14 (s) and 1.24 (s) from DMSO impurity; 2.32(s), 2.5(s) and 2.68(s) from DMSO; 2.9 (t, 2H from —$CH_2$—S—Au); 3.22 (s, 3H from —$OCH_3$); 3.3 (s, broad) from $H_2O$; 3.43(dt, 2H from —$CH_2CH_2S$—AU) and 3.5 (m, 10H) and 3.64 (t, 2H from —$CH_2OCH_3$).

Figure 5A:
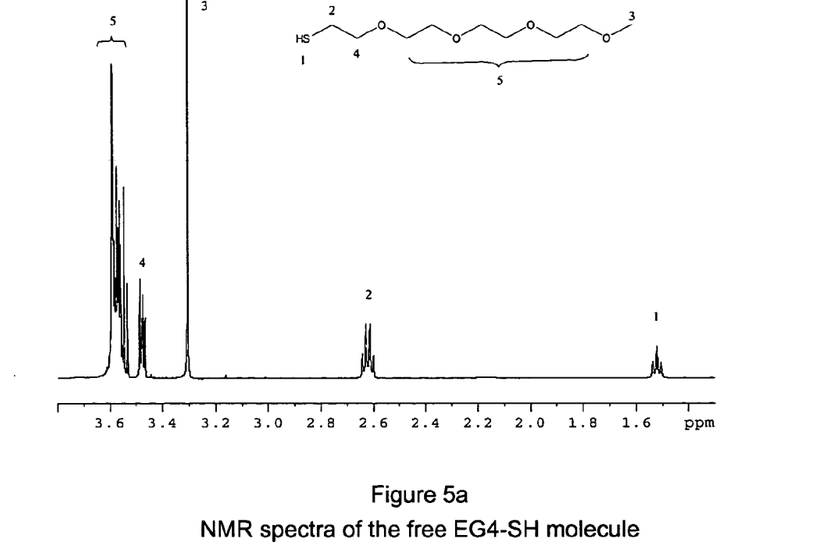
FIG. 5 is a NMR spectra of the free EG4-SH molecule and the Au—S-EG4 nanoparticle.
Figure 5B:
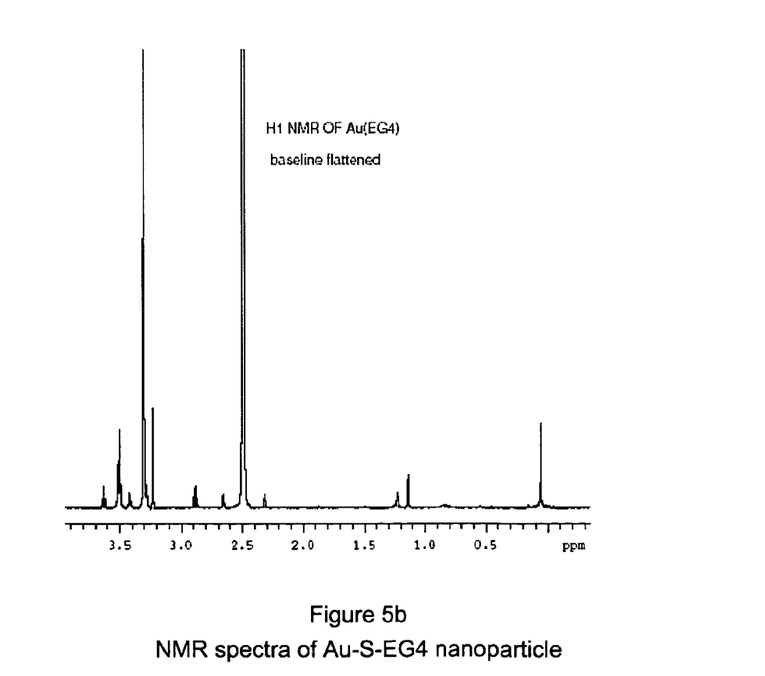

The NMR spectra of both the free EG4-SH molecule and the Au—S-EG4 nanoparticle are shown in FIG. 5. The disappearance of the —SH proton signal (t, 1.50-1.56 ppm) in Au—S-EG4 nanoparticle clearly supports that gold nanoparticle is bonded with EG4-S— monolayer. The chemical shifts and the integrals of the rest protons confirm that the bonded ethylene glycol molecules have the same structure as the free ones.

Example 13

Binding Assay of RNA and DNA

Bacterial *E. coli* wild type cell MG1655 was chosen for this assay. Cell extracts were prepared as follows. Cells were grown in LB rich medium to $OD_{600}$=0.2. Cell membranes were broken by freeze-and-thawing for 3 three times. Total RNA and chromosomal DNA from the *E. coli* cells were purified following standard molecular biology protocols. Binding assays were done by mixing the indicated amount of Au-$EG_4$ particles RNA and DNA at room temperature. After a 10 min incubation, the total volume of the mixture was subjected to gel-electrophoresis, as described in Example 6. The results are shown in FIG. 6.

Figure 6:
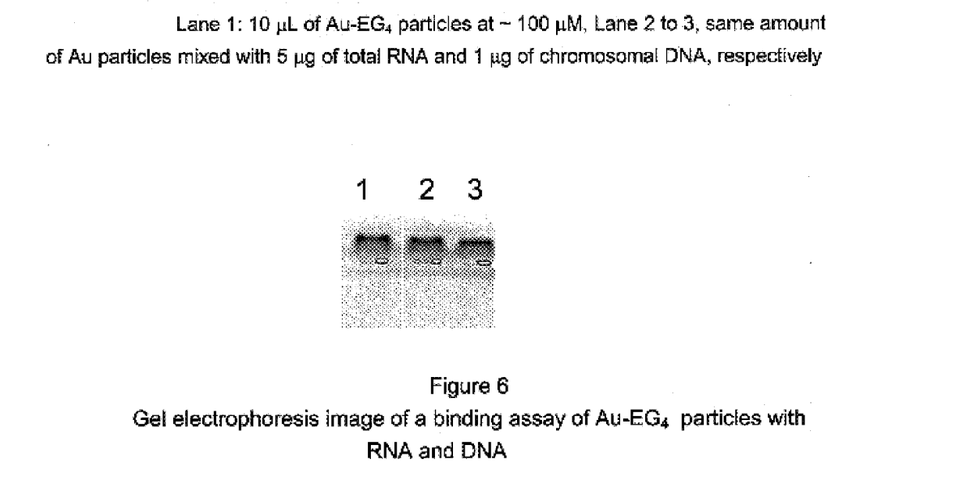
FIG. 6 is a gel electrophoresis image of a binding assay of Au-EG$_4$ particles with RNA and DNA.

AS shown in FIG. 6 both RNA and DNA purified from bacterial cells fail to bind to the Au-EG4 particles. These results illustrate that the particles are resistant to non-specific binding by nucleic acids.

What is claimed is:

1. A process for the preparation of a water soluble metallic nanoparticle coated with a mixed monolayer comprising:
   a) providing;
      i) a metal salt
      ii) a short chain ethylene glycol oligomer shielding component having metal binding functionality;
      iii) a capture coating component having metal binding functionality and having an affinity for a capture moiety;
      iv) a suitable reducing agent; and
      v) a mixed solvent comprising at least one substantially water miscible organic solvent and at least one aqueous solvent wherein the mixed solvent is at a pH of less than 7.0;
   b) mixing elements (i)-(iv) in the mixed solvent of (v) to form a reaction mixture, wherein a mixed monolayer forms on the metallic nanoparticle; and
   c) optionally isolating the mixed monolayer coated metal nanoparticle of (b);

wherein the metallic nanoparticle is selected from the group consisting of gold, silver, platinum, palladium, copper, and alloys composed of these metals.

2. A process according to claim 1 wherein the metal salt is selected from the group consisting of $HAuCl_4$, $AgNO_3$, $Cu(CH_3CO_2)_2$, $Cu(NO_3)_2$, $HPtCl_6$, and $K_2PdCl_4$.

3. A process according to claim 1 wherein the capture moiety is selected from the group consisting of: peptides, proteins, nucleic acid fragments, collagen, nano-rods, nano-tubes, nano-planes and nano-fibers.

4. A process according to claim 1 wherein said capture coating component is selected from the group consisting of
   a) molecules having reactive groups selected from the group consisting of:
      —$NH_2$, —COOH, —CHO—, —OH, —X (Cl, Br, I), succinimide, and epoxy groups; and
   b) biomolecules selected from the group consisting of: peptides; tiopronin and GSH.

5. A process according to claim 1 wherein the metal binding functionality binds metals selected from the group consisting of gold, silver, platinum, palladium, copper, and alloys composed of these metals.

6. A process according to claim 1 wherein said metal binding functionality is an SH group and said metal is gold.

7. A process according to claim 1 wherein said at least one substantially water miscible organic solvent is selected from the group consisting of; $C_1$-$C_6$ alkanols, dimethyl sulfoxide, tetrahydrofuran, dimethylformamide, Dioxane, and acetone.

8. A process according to claim 1 wherein said at least one aqueous based solvent is selected from the group consisting of; water, and acetic acid.

9. A process according to claim 1 wherein said suitable reducing agent is selected from the group consisting of $NaBH_4$, lithium triethylborohydride and hydrogen peroxide.

10. A process according to claim 1 wherein the short chain ethylene glycol oligomer has a molecular weight less than the entanglement molecular weight.

11. A process according to claim 1 wherein the short chain ethylene glycol oligomer is selected from the group consisting of tetraethylene glycol thiol and diethylene glycol thiol.

12. A process according to claim 1 wherein the shielding component comprises at least 50% of the mixed monolayer.

13. A process as recited in claim 1, wherein the final concentration of water in the reaction mixture is from about 5% to about 20% V/V.

14. A process as recited in claim 1, wherein the final concentration of water in the reaction mixture is from about 9% to about 18% V/V.

* * * * *